United States Patent
Sugise et al.

(10) Patent No.: US 6,472,498 B2
(45) Date of Patent: Oct. 29, 2002

(54) DIARYL CARBONATE PRODUCT AND PRODUCTION OF POLYCARBONATE

(75) Inventors: Ryoji Sugise; Shuji Tanaka; Kohichi Kashiwagi; Takashi Doi; Hirofumi Ii; Masayuki Nishio; Shinichi Yoshida; Yutaka Asada; Kazuo Miyamoto, all of Yamaguchi (JP)

(73) Assignee: Ube Industries, Ltd., Yamaguchi (JP)

( * ) Notice: Subject to any disclaimer, the term of this patent is extended or adjusted under 35 U.S.C. 154(b) by 0 days.

(21) Appl. No.: 09/923,466

(22) Filed: Aug. 6, 2001

(65) Prior Publication Data

US 2002/0019512 A1 Feb. 14, 2002

(30) Foreign Application Priority Data

Aug. 4, 2000 (JP) ........................................ 2000-236877
Aug. 4, 2000 (JP) ........................................ 2000-236878

(51) Int. Cl.⁷ .............................................. C08G 64/00
(52) U.S. Cl. ....................................... 528/196; 528/198
(58) Field of Search ................................. 528/196, 198

(56) References Cited

U.S. PATENT DOCUMENTS

| 4,788,273 A | * 11/1988 | Petri ........................... 528/196 |
| 5,239,106 A | 8/1993 | Shafer ......................... 558/274 |
| 5,648,510 A | 7/1997 | Harada et al. |
| 5,892,091 A | 4/1999 | Harada et al. |
| 5,922,827 A | 7/1999 | Nishihira et al. ........... 528/196 |
| 6,265,524 B1 | 7/2001 | Takemoto et al. ........... 528/196 |

FOREIGN PATENT DOCUMENTS

| EP | 0 722 931 A1 | 7/1996 |
| GB | 1096936 | 2/1965 |

* cited by examiner

Primary Examiner—Terressa M. Boykin
(74) Attorney, Agent, or Firm—Reed Smith LLP

(57) ABSTRACT

A composition consisting essentially of a diaryl carbonate and contains a furan ring-containing compound in an amount of not more than 1 ppm is favorably employable for producing less colored polycarbonate.

20 Claims, 3 Drawing Sheets

DIARYL CARBONATE PRODUCT AND PRODUCTION OF POLYCARBONATE

CROSS-REFERENCES TO RELATED APPLICATIONS

This application claims priority of Japanese Application Nos. 2000-236877 filed Aug. 4, 2000 and 2000-236878 filed Aug. 4, 2000, the complete disclosure of which are hereby incorporated by reference.

FIELD OF THE INVENTION

The invention relates to a diaryl carbonate product containing little impurities and a process for production of polycarbonate from the diaryl carbonate product.

BACKGROUND OF THE INVENTION

Diaryl carbonate is known as a starting compound for producing a variety of chemical compounds, particularly, polycarbonate. For the production of polycarbonate, a diaryl carbonate is reacted with a polyhydric aromatic compound such as a bisphenol compound under polycondensation reaction in the presence of a catalyst.

The polycarbonate has excellent property in mechanical strength, transparency, electric characteristics, and optical characteristics, and is widely employed, for instance, for producing substrate of compact discs and other electric and electronic materials, organic glassy materials, and optical lenses.

There are known various processes for preparing a diaryl carbonate such as transesterification of dialkyl carbonates and reaction of phosgene and a phenol compound.

Recently, a process for producing a diaryl carbonate by decarbonylation of a diaryl oxalate has been invented as is described in U.S. Pat. No. 5,648,510. Further, U.S. Pat. No. 5,892,091 teaches that the decarbonylation of a diaryl oxalate is favorably performed in the presence of such a catalyst as an organic phosphorus compound.

U.S. Pat. No. 5,922,827 describes a process for producing polycarbonate from a diaryl carbonate prepared by decarbonylation of a diaryl oxalate.

SUMMARY OF THE INVENTION

The present inventors have studied to employ the diaryl carbonate prepared by the decarbonylation of a diaryl oxalate for producing a polycarbonate by reacting it with a polyhydric compound. In the course of the study, the inventors have noted that the polycarbonate produced by the use of a diaryl carbonate prepared by the decarbonylation of a diaryl oxalate is likely colored to have a yellow color. The colored polycarbonate is disadvantageous particularly in the case that the polycarbonate is employed for producing optical elements such as optical discs and optical lenses.

Therefore, the inventors have studied further to find causes by which the polycarbonate is colored. As a result, they have discovered that a furan ring-containing compound is contained in the diaryl carbonate-containing reaction product obtained by the decarbonylation, and that the furan ring-containing compound colors the resulting polycarbonate yellow, even if the amount of the furan ring-containing compound is very small. A representative furan ring-containing compound is benzofuran-2,3-dione which is assumed to be produced by Fries rearrangement of the diaryl oxalate.

It is then confirmed that a less colored polycarbonate resin can be produced when a diaryl carbonate product of which furan ring-containing compound content is decreased to a level of less than 1 ppm (wt. ppm) is employed for the production of polycarbonate.

Accordingly, the present invention resides in a composition comprising a diaryl carbonate and a furan ring-containing compound in an amount of not more than 1 ppm (by weight). The composition of the invention is preferably derived from a reaction mixture of decarbonylation reaction of a diaryl oxalate.

A representative furan ring-containing compound is benzofuran-2,3-dione or its derivative which is assumed to have been derived from the diaryl oxalate via side-reaction.

The invention further resides in a process favorably employable for preparing the composition of the invention containing little amount of the by-produced furan ring-containing compound, which comprises the steps of:

recovering from the reaction mixture of decarbonylation, a first distillate comprising a diaryl carbonate, a furan ring-containing compound, an unreacted diaryl oxalate, and other by-products, by distillation (or evaporation);

recovering from the first distillate, a second distillate comprising a diaryl carbonate in an amount of not less than 95.0 wt. %, a furan ring-containing compound in an amount of 1 to 2,000 ppm, and an unreacted diaryl oxalate in an amount of not more than 1 wt. %, by distillation; and removing from the second distillate at least a portion of the furan ring-containing compound.

The invention further resides in a process for preparing polycarbonate which comprises reacting a polyhydric compound with a composition of the invention comprising a major portion of a diaryl carbonate and a furan ring-containing compound in an amount of not more than 1 ppm.

DETAILED DESCRIPTION OF THE INVENTION

It is preferred that the content of a furan ring-containing compound (hereinafter referred to as "furan derivative") in the composition of the invention which is derived from a reaction mixture of decarbonylation reaction of a diaryl oxalate is as low as possible. However, it is not easy to completely remove the furan derivative from the reaction mixture in an industrially employable process. According to the studies of the present inventors, it has been confirmed that if the content of the furan derivative in the product consisting essentially of a diaryl carbonate is not more than 1 ppm, the troublesome coloring of polycarbonate produced by the use of the diary carbonate product is effectively obviated. The content of a furan derivative preferably is not more than 0.8 ppm, more preferably in the range of 10 ppb to 0.5 ppm. Most preferred is that the content of the furan derivative is less than 0.3 ppm.

It is further preferred that the diaryl carbonate product contains little hydrolyzable halide (particularly chloride) compounds, preferably 0.2 ppm or less in terms of a halogen (particularly chlorine) content. The halogen content preferably is in the range of 1 ppb to 0.1 ppm, more preferably is in the range of 5 to 50 ppb.

It is also preferred that the diaryl carbonate product contains little organic halide compounds other than the hydrolyzable halide compounds, preferably 10 ppm or less, particularly in the range of 50 ppb to 5 ppm, in terms of a halogen content.

The hydrolyzable halide compounds and organic halide compounds are assumed to have been brought about into the reaction mixture as contaminants derived from a decarbonylation catalyst or an auxiliary catalyst compound.

It is further preferred that the composition of the invention (i.e., diaryl carbonate product) comprises a diaryl carbonate in an amount of 98 wt. %. The composition of the invention comprises a diaryl carbonate, more preferably in an amount of 99.0 wt. % or higher, most preferably 99.30 wt. % or higher (probably up to 99.9 wt. %).

A diaryl oxalate which is an unreacted starting compound is likely contained in the reaction mixture and incorporated into the composition of the invention. The content of diaryl oxalate in the composition of the invention preferably is not more than 2,000 ppm.

Figure 1:
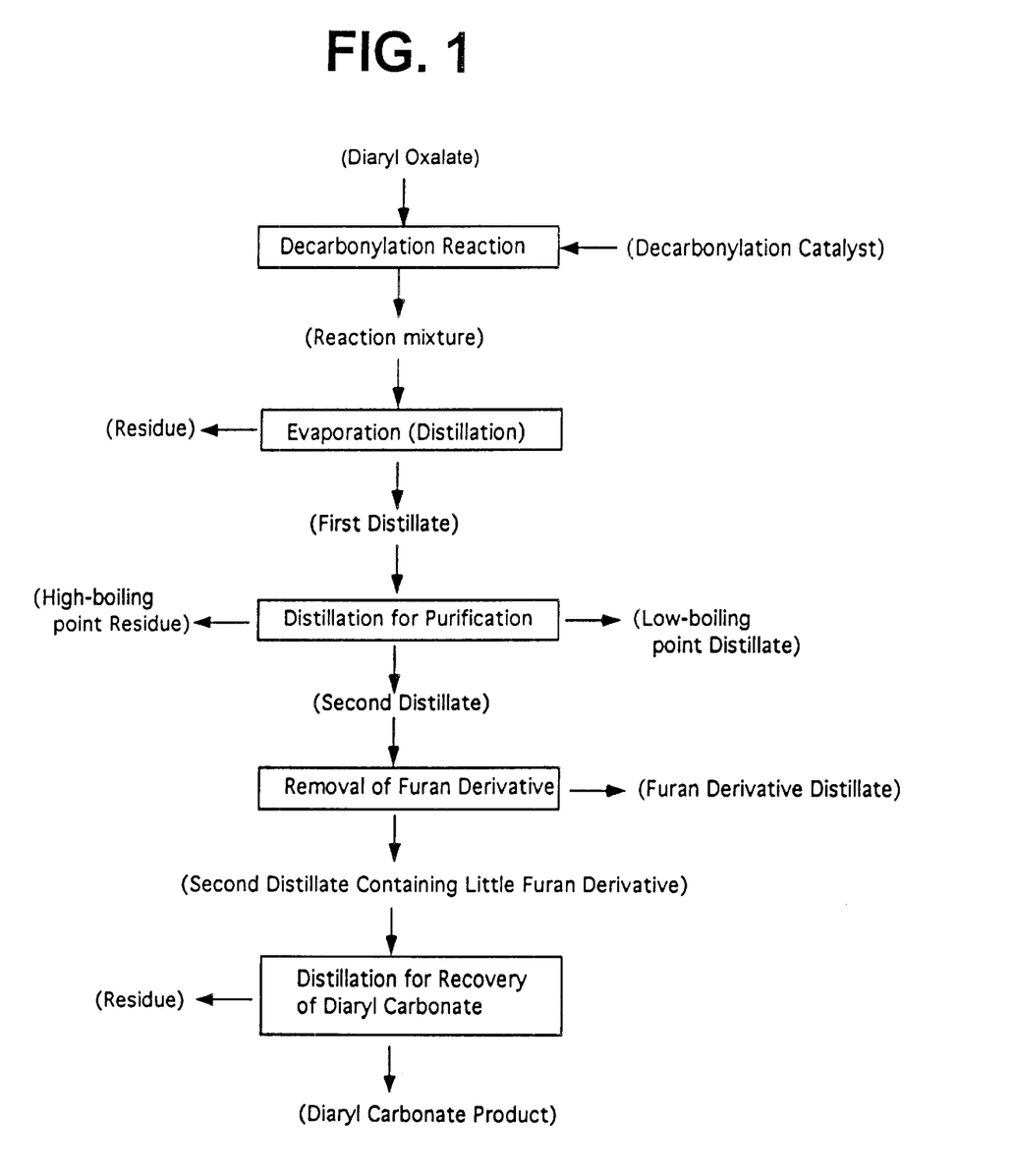
FIG. 1 is a flow chart of a process of the invention which is favorably employable for preparing a diaryl carbonate product containing little impurities from a reaction mixture of decarbonylation of a diaryl oxalate.

The diaryl carbonate composition of the invention can be prepared from the reaction mixture of decarbonylation reaction of a diaryl oxalate after subjecting the reaction mixture to specific purification processes. A flow chart of a representative process of the invention for obtaining a diaryl carbonate product of extremely high purity is illustrated in FIG. 1.

The decarbonylation reaction of a diary oxalate proceeds in the following reaction scheme (1):

In the reaction scheme (1), each of $Ar^1$ and $Ar^2$ is the same or different aryl or aralkyl group, which may have one or more substituents. A representative aryl group is phenyl. Examples of the substituents include an alkyl group having 1 to 12 carbon atoms (e.g., methyl, ethyl, or propyl), an alkoxy group having 1 to 12 carbon atoms (e.g., ethoxy, methoxy, or propoxy), a halogen atom (e.g., fluorine atom or chlorine atom) and a nitro group. A representative diaryl oxalate is diphenyl oxalate which can have one or more substituents on its phenyl moiety.

The by-produced carbon monoxide is taken out from the reaction mixture in the form of gas. If desired, the gaseous carbon monoxide is collected for the use in various chemical reactions.

The decarbonylation reaction of a diaryl oxalate is preferably performed in liquid phase in the presence of a decarbonylation catalyst such as an organic phosphorus catalyst, most preferably a phosphonium catalyst.

The details of the decarbonylation reaction and the preferred catalysts are described in the aforementioned U.S. Pat. Nos. 5,648,510 and 5,892,091.

In the decarbonylation reaction, the organic phosphorus catalyst can be employed in an amount of 0.001 to 50 mol. %, preferably 0.01 to 20 mol. %, based on the amount of the diaryl oxalate. The catalyst can be dissolved in the diaryl oxalate. Otherwise, at least a portion of the catalyst is dissolved in the diaryl oxalate. An auxiliary catalyst component can be employed in combination with the organic phosphorus catalyst.

The reaction mixture of decarbonylation generally comprises the produced diaryl carbonate (generally in an amount of 50 to 95 wt. %), an unreacted diaryl oxalate, the catalyst, a by-produced furan ring-containing compound (i.e., furan derivative), and other by-products such as products having a higher or lower boiling point.

The reaction mixture of decarbonylation is distilled or evaporated for the purpose of separating the produced diaryl carbonate from the catalyst composition. The distillation or evaporation can be performed in known distilling apparatuses or evaporators. An evaporator of flowing-down film type and a thin-film evaporator are favorably employed.

In the distillation or evaporation, the reaction mixture can be heated to a temperature in the range of approx. 100 to 250° C., preferably 130 to 200° C., which is similar to the reaction temperature of the decarbonylation reaction under a reduced pressure in the range of approx. 0.1 to 50 kPaA, preferably approx. 0.2 to 20 kPaA, so as to recover a gaseous mixture comprising the desired diaryl carbonate, an unreacted diaryl oxalate, and by-products having a low boiling point.

The gaseous mixture gives a first distillate which preferably contains approx. 70 to 95 wt. % of a diaryl carbonate and approx. 5 to 25 wt. % of a diaryl oxalate. The total amount of a diaryl carbonate and a diaryl oxalate in the gaseous mixture preferably is in the range of 80 to 99.9 wt. %, more preferably 85 to 99.0 wt. %. The gaseous mixture further contains approx. 0.1 to 5 wt. % of various by-products. The by-products comprise by-produced materials having a boiling point lower than that of the diaryl carbonate, such as phenol and a furan derivative and by-produced materials having a boiling point higher than that of the diaryl carbonate. The gaseous mixture preferably contains almost no components derived from the decarbonylation catalyst.

A representative example of the furan ring-containing compound is benzofuran-2,3-dione or its derivative which is assumed to have been by-produced from the diaryl oxalate or its derivative by Fries rearrangement reaction in the following mechanism (2):

In the above-illustrated formulas, R is a substituent of the phenyl group of a diaryl oxalate, corresponding to $Ar^1$ and $Ar^2$ of the aforementioned formula (1).

After the reaction mixture of decarbonylation reaction is evaporated, a mixture of catalyst components (e.g., phosphonium salt components derived from the phosphonium catalyst), a non-evaporated diaryl carbonate, a non-evaporated diaryl oxalate, and other by-products having a boiling point higher than that of the diaryl carbonate remains in the evaporation apparatus. The residual mixture can be returned to a mixture of a diaryl oxalate and a catalyst for decarbonylation. If the residual mixture is returned to the decarbonylation system, a halide compound such as hydrogen chloride, an alkane halide, an aralkyl halide, a halogen-substituted aliphatic carboxylic acid, a carboxylic halide, or sulfonic chloride can be added to the residual mixture or the decarbonylating mixture in an amount of 0.1 to 100 mol. %, based on the amount of the organic phosphorus catalyst component in the residual mixture, so as to activate the returned catalyst component.

The evaporated mixture (i.e., first distillate) is then distilled for purification, that is, to remove low-boiling point compounds and high-boiling point compounds and to recover a second distillate preferably comprising the diaryl carbonate in an amount of not less than 95.0 wt. %, the furan ring-containing compound in an amount of 1 to 2,000 ppm, and the unreacted diaryl oxalate in an amount of not more than 1 wt. %.

Examples of the low-boiling point compounds include phenolic compounds such as phenol and cresol and furan ring-containing compounds, which have a boiling point lower than that of the diaryl carbonate. Examples of the high-boiling point compounds include the diaryl oxalate, methyphenylphenyl oxalate, phenyl p-chlorobenzoate, and phenyl salicylate which are the starting compound, contaminants of the starting compound, or by-products produced in the decarbonylation reaction and the evaporation procedure.

The distillation for obtaining the second distillate can be performed in the following manner:

1) the first distillate is distilled to remove a distillate comprising a diaryl carbonate and low boiling point impurities such as phenol derivatives to leave a residue comprising a major portion of a diaryl carbonate and a reduced amount of low boiling point impurities; and 2) the residue is then distilled to collect a distillate (i.e., the second distillate) comprising a major portion of a diaryl carbonate and a reduced amount of high boiling point impurities.

The finally obtained distillate preferably comprises a diaryl carbonate in an amount of 96 wt. % or more, more preferably 96 to 99.9 wt. %, most preferably 98.0 to 99.9 wt. %. The residue of the distillation 2) above, which comprises a diaryl oxalate, a diaryl carbonate, and high boiling point by-products, can be returned to the decarbonylation procedure.

The second distillate generally contains a diaryl oxalate in an amount of approx. 1 ppm to 1 wt. %, particularly 10 to 2,000 ppm, and furan derivatives such as benzofuran-2,3-dione in an amount of 0.1 to 2,000 ppm, particularly 1 to 2,000 ppm.

The second distillate is subsequently subjected to another purification process for removing most of the furan derivatives, so as to obtain the desired diaryl carbonate product comprising a diaryl carbonate of approx. 99.00 wt. % or more, particularly 99.30 to 99.9 wt. %, more particularly 99.50 to 99.99 wt. %, and contains little furan derivatives such as in an amount of approx. 5 ppb to 0.8 ppm, particularly 10 ppb to 0.5 ppm, more particularly 10 ppb to 0.3 ppm.

In the furan derivative-removing process, the second distillate can be subjected to one of the following procedures:

a) distillation b) heat treatment and subsequent distillation c) hydrogenation and subsequent distillation d) adsorption The distillation a) of the second distillate is performed in a known manner for further removing the furan derivatives to the desired diaryl carbonate product containing the furan derivative in an amount of not more than 1 ppm.

The heat treatment and subsequent distillation b) can be performed by heating the second distillate to decompose, condensate and/or modify the furan derivative and subsequently distilling thus heat treated second distillate to recover the desired diaryl carbonate product of high purity, leaving the products of decomposition, condensation and/or modification which generally have a boiling point higher than that of a diaryl carbonate. Thus obtained diaryl carbonate product contains the furan derivative in an amount of not more than 1 ppm, and preferably comprises a diary carbonate in an amount of 99.50 wt. % or more.

The heat treatment of the second distillate can be performed at a temperature in the range of 150 to 300° C., preferably 180 to 250° C., more preferably 200 to 230° C., for a period of 0.05 to 10 hours, preferably 0.1 to 5 hours, so as to decompose, condensate and/or modify most (80% or more, particularly 90% or more, most particularly 95% or more) of the furan derivative.

If desired, the diaryl carbonate product obtained by the distillation a) or the combination of heat treatment and subsequent distillation b) can be further distilled to recover a diaryl carbonate product of higher purity. By the present distillation, high boiling by-products such as organic halide compounds (e.g., phenyl p-chlorobenzoate) other than hydrolyzable halide compounds are left in the residue, to give a diaryl carbonate product containing the hydrolyzable halide compounds (e.g., hydrolyzable organic halide compounds such as phenyl chloroformate and hydrolyzable inorganic halide compounds such as hydrochloric acid) in an amount of not more than 0.2 ppm, particularly 1 ppb to 0.1 ppm, more particularly 5 to 50 ppb in terms of halogen atom content, and other organic halide compounds such as phenyl p-chlorobenzoate in an amount of not more than 10 ppm, particularly 10 ppb to 5 ppm in terms of halogen atom content.

Figure 2:
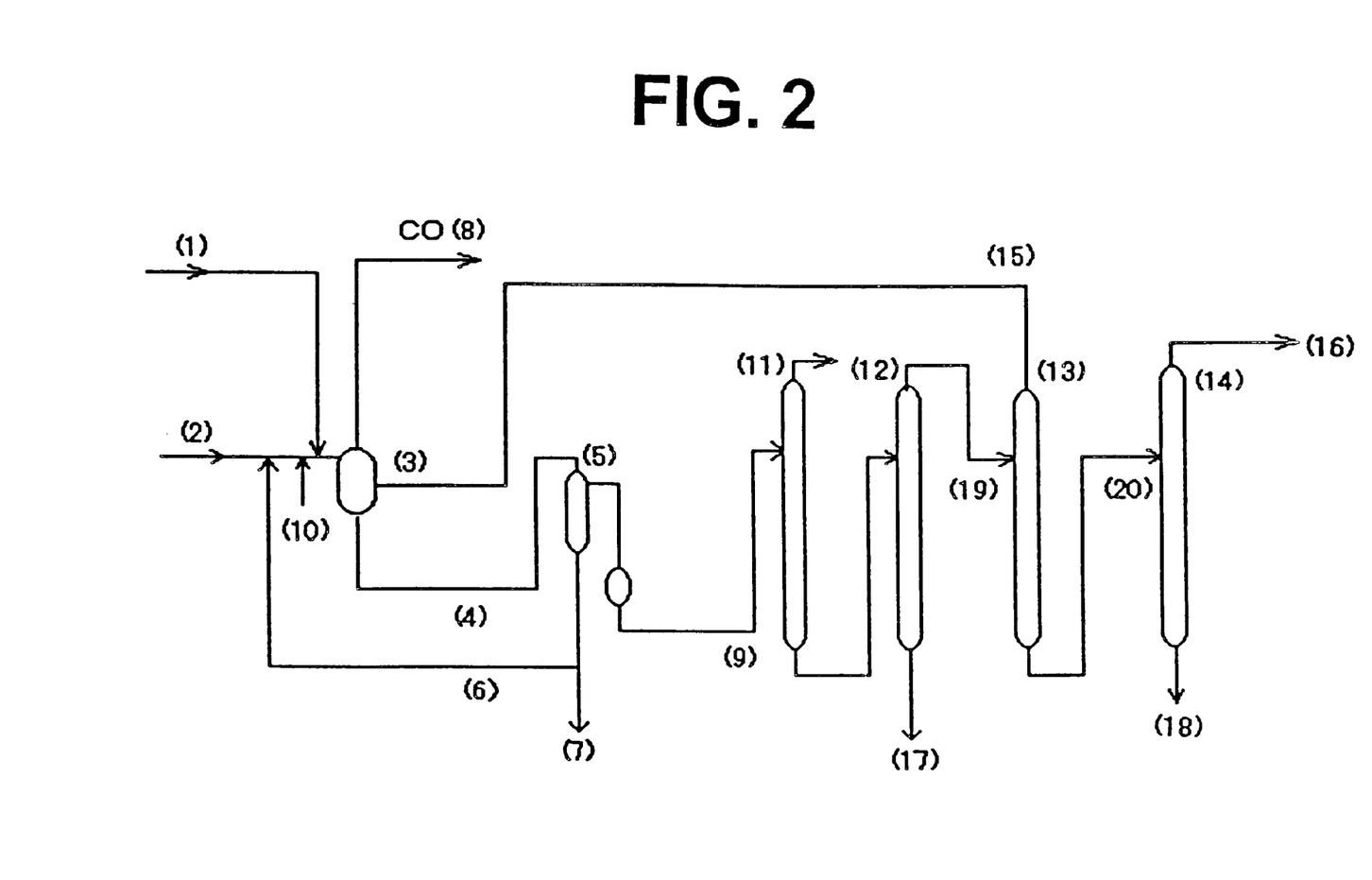
FIG. 2 is a process chart which is favorably employable for preparing a diaryl carbonate product of the invention containing little impurities.

FIG. 2 illustrates a series of apparatuses employable for obtaining a diaryl carbonate product of high purity.

In FIG. 2, a decarbonylation catalyst and a diaryl oxalate are supplied to a decarbonylation reactor (3) through line (1) and line (2), respectively. In the reactor (3), the decarbonylation reaction of diaryl oxalate is carried out in liquid phase at a temperature of 100 to 450° C. (preferably 160 to 400° C., more preferably 180 to 350° C.) at a pressure of 10 mmHg to 10 kg/cm$^2$ (particularly, at a pressure of 100 mmHg to 8 kg/cm$^2$) for a period of approx. 0.5 to 20 hours (particularly 1 to 10 hours). Carbon monoxide produced in the decarbonylation reaction is taken out to the outside through line (8).

The reaction mixture is taken out from the reactor (3) through line (4) and supplied into an evaporator (5). In the evaporator (5), the reaction mixture is heated under reduced pressure to produce a distillate (i.e., first distillate). The first distillate is collected and supplied to a distillation tower (11) through line (9). The residue which is produced in the evaporator (5) and contains the decarbonylation catalyst is preferably returned to the decarbonylation reactor (3) through a combination of line (6) and the line (2). It is preferred that almost all of the residue (e.g., 90 to 99.99 wt. %) is returned to the decarbonylation reactor (3). A halogen-containing compound is preferably supplemented to the returning residue through line (10) so as to activate the decarbonylation catalyst contained in the residue. A portion of the residue (for instance, 0.05 to 5 wt. %) taken out from the evaporator (5) can be taken out to the outside through line (7), so as to remove a portion of by-produced high-boiling point products.

In the distillation tower (11), the first distillate is placed under reduced pressure to distill by-produced low-boiling point products out. The residue is then supplied to another distillation tower (12).

In the distillation tower (12), the residue is placed under reduced pressure to collect the second distillate consisting essentially of a diaryl carbonate by distillation. The second distillate is subsequently supplied to a further distillation tower (13) (mainly for removing the furan derivative) through line (19). The residue produced in the distillation tower (12) is taken out through line (17). The residue taken out through the line (17) contains an unreacted diaryl oxalate, and therefore the residue is preferably returned to the decarbonylation reactor (3).

In the distillation tower (13), a furan derivative-containing distillate is removed through line (15). If the furan derivative-containing distillate contains a certain amount of a diaryl carbonate, the distillate can be returned to the reactor (3). The residue left in the distillation tower (13) consisting essentially of a diaryl carbonate and contains almost no furan derivatives.

However, if the content of furan derivatives in the residue of the distillation tower (13) is not satisfactorily low, the residue can be further subjected to distillation. In this case, the residue is supplied to a still further distillation tower (14) through line (20).

In the distillation tower (14), the residue is placed under reduced pressure to collect a diaryl carbonate distillate thorough line (16). The residue left in the distillation tower (14) contains high-boiling point products and taken out to the outside through line (18).

Figure 3:
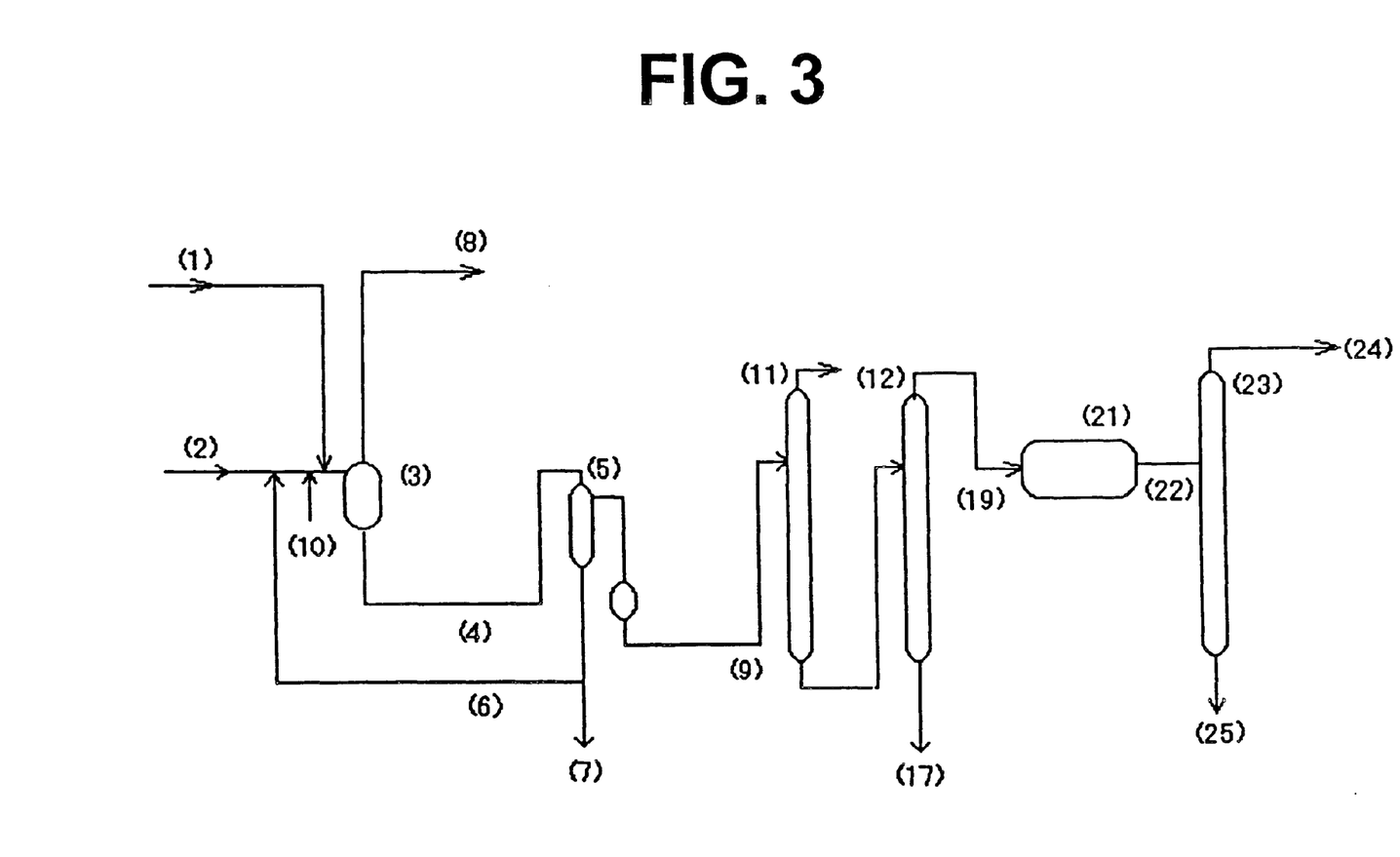
FIG. 3 is another process chart which is also favorably employable for preparing a diaryl carbonate product of the invention containing little impurities.

FIG. 3 illustrates another series of apparatuses employable for obtaining a diaryl carbonate product of high purity. The apparatuses of FIG. 3 essentially differs from those of FIG. 2 in the replacement of the distillation tower (13) (for removal of the furan derivative) with a heating apparatus (21) for decomposing, condensating, and/or modifying the furan derivatives in the second distillate. Thus heat-treated second distillate is then supplied to the distillation tower (23) through line (22).

In the distillation tower (23) of FIG. 3, the residue is placed under reduced pressure to collect a diaryl carbonate distillate thorough line (24). The residue left in the distillation tower (23) contains high-boiling point products and taken out to the outside through line (25).

The diaryl carbonate product containing almost no furan derivatives is favorably employed in combination with a polyhydric compound to produce polycarbonate having little color by polycondensation reaction.

The polycondensation reaction between a diaryl carbonate and a polyhydric compound for producing polycarbonate per se is well known.

A representative polyhydric compound is an aromatic polyhydric compound in which a plurality (particularly, two) of hydroxyl groups are directly attached to an aromatic ring of an aromatic compound. The aromatic polyhydric compound can be employed in combination with an aliphatic polyhydric compound (e.g., aliphatic diol compound such as ethylene glycol, propylene glycol, butane diol or hexane diol), provided that at least 60 mol. % of the mixture, preferably at least 80 mol. % of the mixture, is an aromatic polyhydric compound.

Examples of the aromatic polyhydric compounds include bis(hydroxyaryl)alkanes (which are called bisphenol type compounds) such as bis(4-hydroxyphenyl)methane, 1,1-bis (4-hydroxyphenyl)ethane, 2,2-bis(4-hydroxyphenylbutane), 2,2-bis(4-hydroxyphenyl)octane, bis(4-hydroxyphenyl) phenylmethane, 2,2-bis(4-hydroxy-2-methylphenyl) propane, 1,2-bis(4-hydroxy-2-t-butylphenyl)propane, and 2,2-bis(4-hydroxy-3-bromophenyl)propane; hydroxyaryl ethers such as 4,4'-dihydroxydiphenyl ether and 4,4'-dihydroxy-3,3'-dimethyldiphenyl ether; dihydroxyaryl sulfides such as 4,4'-dihydroxydiphenyl sulfide and 4,4'-dihydroxy-3,3'-dimethyldiphenyl sulfide; dihydroxyaryl sulfoxides such as 4,4'-dihydroxydiphenyl sulfoxide and 4,4'-dihydroxy-3,3'-dimethyldiphenyl sulfoxide; and dihydroxyaryl sulfones such as 4,4'-dihydroxydiphenyl sulfone and 4,4'-dihydroxy-3,3'-dimethyldiphenyl sulfone.

In the production of polycarbonate, a diaryl carbonate of high purity is preferably employed in an amount of 1.001 to 1.5 mol., particularly 1.01 to 1.3 mol., per one more of the polyhydric compound such as an aromatic dihydric compound. In the production, a polymerization regulator, a terminal group-modifying agent and a monophenol compound may be employed in addition to the diaryl carbonate and polyhydric compound.

For the production of polycarbonate, an appropriate basic catalyst (e.g., organic acid salt, inorganic acid salt, hydroxide, hydride, or alcoholate of an alkali metal or an alkaline earth metal, or an nitrogen atom-containing basic compound) is generally employed. For instance, the production is carried out by heating a mixture of an aryl carbonate, a polyhydric compound and a basic catalyst to a temperature of approx. 100 to 330° C., removing a by-produced phenol compound by evaporation. The reaction temperature is preferably increased gradually and the pressure is decreased gradually. The polymerization reaction is preferably performed in one step or in two steps.

Examples of the basic catalysts for producing polycarbonates include the following:

(1) Nitrogen Atom-containing Basic Compounds ammonium hydroxides having alkyl, aryl, or aralkyl group (e.g., tetraethylammonium hydroxide, tetraethylammonium hydroxide, tetrabutylammonium hydroxide, and trimethylbenzylammonium hydroxide; tertiary amines (e.g., trimethylamine, triethylamine, dimethylbenzylamine, and triphenylamine); secondary amines; primary amines, tetramethylammonium borohydride; and tetrabutylammonium borohydride (2) Alkali Metal Compounds alkali metal hydroxides (e.g., sodium hydroxide, potassium hydroxide, and lithium hydroxide); alkali metal hydrogen carbonates (e.g., sodium hydrogen carbonate, potassium hydrogen carbonate, and lithium hydrogen carbonate); alkali metal carbonates (e.g., sodium carbonate, potassium carbonate, and lithium carbonate); and alkali metal phosphates and phosphites (e.g., sodium dihydrogen phosphate, potassium dihydrogen phosphate, lithium dihydrogen phosphate, potassium dihydrogen phosphite, sodium dihydrogen phosphite, disodium hydrogen phosphate, dipotassium hydrogen phosphate, and dilithium hydrogen phosphate); organic acids of alkali metal (e.g. sodium acetate, potassium acetate, lithium acetate, sodium stearate, and sodium benzoate); alkali metal hydrides (e.g., sodium borohydride); and alkali metal alcoholates (e.g., sodium phenolate)

(3) Alkaline Earth Metal Compounds alkaline earth metal hydroxides (e.g., calcium hydroxide, barium hydroxide, and magnesium hydroxide); alkaline earth metal hydrogen carbonates (e.g., calcium hydrogen carbonate, barium hydrogen carbonate, and magnesium hydrogen carbonate); alkaline earth metal carbonates (e.g., calcium carbonate, barium carbonate, and magnesium carbonate); and organic acid salts of alkaline earth metal (e.g., calcium acetate, barium acetate, barium stearate, and magnesium stearate).

The basic catalysts can be employed alone or in combination.

The basic catalyst can be employed in the production of polycarbonate in an amount of $10^{-8}$ to $10^{-1}$ mol., particularly $10^{-7}$ to $10^{-2}$ mol., per one mol. of the polyhydric compound.

The polycondensation reaction for the production of polycarbonate can be performed in the conventional manner. For instance, in the first step, the polycondensation reaction is performed between a polyhydric compound (specifically, aromatic dihydric compound) and a diaryl carbonate at a temperature of 80 to 250° C. (preferably 100 to 230° C., more preferably 150 to 200° C.) for a period of 0.01 to 5 hours (preferably 0.05 to 4 hours, more preferably 0.25 to 3 hours) under atmospheric pressure or reduced pressure. In the second step, the polycondensation reaction is performed at an elevated temperature and under more reduced pressure, and finally the reaction is preferably carried out at 240 to 320° C. at a pressure of 1 mmHg or less.

The polycondensation reaction can be carried out continuously or in a batch system.

The diaryl carbonate product of the invention having an extremely high purity can be polycondensated with a polyhydric compound in a conventional melt polymerization method to give polycarbonate having a high molecular weight 10,000 to 80,000, which is similar to the known polycarbonate. The polycarbonate of the invention also has well acceptable properties. It is then stressed that polycarbonate produced using a diaryl carbonate product of the invention has almost no color and therefore is very advantageous in industrial uses such as uses for manufacturing optical discs and transparent lenses.

The present invention is further described by the following examples. In the examples, the analyses of the reaction mixture and the chemical compositions were carried out by liquid chromatography. The analytical limits of the liquid chromatography vary dependent upon the natures of chemical species, but generally are approx. 0.1 to 1 ppm.

EXAMPLE 1

Diphenyl oxalate was subjected to decarbonylation reaction and the produced diphenyl carbonate was purified in the series of apparatuses illustrated in FIG. 2.

(1) Decarbonylation of Diphenyl Oxalate

In a 250 L-volume decarbonylation reactor composed of connected two glass-lined stirring vessels (two vessels were connected by an over-flowing pipe), diphenyl oxalate and tetraphenylphosphonium chloride (1.5 wt. %, based on the amount of diphenyl oxalate) were placed, and the reactor was heated by flowing a heating medium into a jacket placed over the reactor. In the reactor, the mixture was stirred to carry out decarbonylation reaction. When the conversion ratio in the first vessel reached approx. 60% and the conversion ration in the second vessel reached approx. 80%, continuous feeding of diphenyl and tetraphenylphosphonium chloride (1.5 wt. %, based on the amount of diphenyl oxalate) into the first vessel was started. In the decarbonylation procedure, the first and second vessels were kept at 225° C. (inner temperature) for maintaining the reaction temperature at the same temperature.

(2) Evaporation of Decarbonylation Reaction Mixture

The reaction mixture in the decarbonylation reactor was taken out and fed into a 100 L-volume glass-lined evaporator. The evaporator was heated by flowing steam through a jacket on the evaporator. In the evaporator, the reaction mixture was placed at a reduced pressure of 1.8 kPaA to evaporate diphenyl carbonate, and other distillates. The distillate (i.e., first distillate) collected from the reaction mixture was composed of 88.54 wt. % of diphenyl carbonate, 9.71 wt. % of diphenyl oxalate, and 1.75 wt. % of impurities.

The residue in the evaporator which contained phosphonium salt components derived from the decarbonylation catalyst was taken out of the evaporator, and most of the residue was returned to the decarbonylation reactor. A portion of the residue was separated out to the outside, so as to adjust the contents of components of the returning residue. Simultaneously with returning the residue, chloroform (in an amount of approx. 10 mol. %, based on the amount of the phosphonium salt components in the returned reside) is supplied into the reactor.

(3) Distillation for Purification

The first distillate was cooled and converted into a liquid which was then placed in a receiver. The first distillate in the form of liquid was then fed into a distillation tower (height: 7 m, diameter: 100 cm (A), column: Merapack 500Y, available from Sumitomo Heavy Machine Co., Ltd., length of column: 5 m). The pressure of the top of the distillation tower was reduced to 6 kPaA, and products of low-boiling point containing phenol was distilled out from the top. The liquid residue at the bottom of the tower was taken out from the bottom. The liquid residue was composed of 88.61 wt. % of diphenyl carbonate, 9.71 wt. % of diphenyl oxalate, and 1.67 wt. % of impurities.

The liquid residue was then fed into another distillation tower (height: 8 m, diameter 250 cm (A), column: Merapack 500Y, length of column: 6 m). The pressure of the top of the distillation tower was reduced to 2.2 kPaA, and a distillate (i.e., second distillate) containing 99.9 wt. % of diphenyl carbonate was collected from the top at a rate of approx. 43 kg/hr. Simultaneously, the liquid residue at the bottom of the tower which contained diphenyl oxalate was taken out from the bottom at a rate of approx. 7 kg/hr.

The second distillate of diphenyl carbonate contained 20 ppm of diphenyl oxalate, 150 ppm of phenyl p-chlorobenzoate, and 2 ppm of benzofuran-2,3-dione. A Hazen color value of the second distillate was 10 to 20.

The liquid residue taken out from the bottom was composed of 46.74 wt. % of diphenyl carbonate, 48.46 wt. % of diphenyl oxalate, and 4.63 wt. % of impurities.

(4) Removal of Furan Derivatives

The second distillate was fed into a further distillation tower (height: 8 m, diameter 200 cm (A), column: Merapack 500Y, length of column: 5 m). The pressure of the top of the distillation tower was reduced to 2 kPaA, and a diphenyl oxalate distillate containing approx. 0.02 wt. % of benzofuran-2,3-dione was as continuously collected at a rate of 0.4 kg/hr., and at a reflux ratio of 20 (i.e., second distillate). Simultaneously, the liquid residue of diphenyl carbonate at the bottom of the tower which contained benzofuran-2,3-dione of 0.2 ppm or less was taken out from the bottom at a rate of approx. 43 kg/hr. A Hazen color value of the second distillate was lower than 5.

(5) Further Purification (Distillation for Recovery of Diaryl Carbonate)

The diphenyl carbonate residue obtained above was fed into a distillation tower (height: 10 m, diameter 250 cm (A), column: Merapack 500Y, length of column: 8 m). The pressure of the top of the distillation tower was reduced to 4 kPaA, and a diphenyl carbonate distillate (diphenyl carbonate content (purity): 99.95%) containing less than approx. 0.2 ppm of benzofuran-2,3-dione was continuously collected at a rate of approx. 42 kg/hr.

Liquid chromatography analysis carried out on the diphenyl carbonate distillate confirmed that no peaks assignable to phenyl p-chlorobenzoate and diphenyl oxalate were detected.

A Hazen color value of the diphenyl carbonate distillate was lower than 5.

A portion of the diphenyl carbonate distillate was burned in a chlorine content analytical apparatus (TOX-10Σ, available from Mitsubishi Chemicals Co., Ltd.) to determine the total chlorine content. The total chlorine content was less than 0.3 ppm. Further, a portion of the diphenyl carbonate distillate was analyzed to determine the chlorine ion content by ion chromatography. The chlorine ion derived from hydrolyzable chlorides. The chlorine ion content was 10 ppb.

Comparison Example 1

The procedures of Example 1 were repeated except that the second distillate was not subjected to the procedure for removal of furan derivative and directly subjected to the further (final) purification procedure.

As a result, a diphenyl carbonate distillate (purity: 99.95%) containing 2 ppm of benzofuran-2,3-dione was continuously collected at a rate of approx. 42 kg/hr.

A Hazen color value of the diphenyl carbonate distillate was 10 to 20.

EXAMPLE 2

A diphenyl carbonate distillate which was finally obtained after a series of the procedures of Example 1 was employed for the production of polycarbonate. The diphenyl carbonate distillate contained 30 ppm of water, 70 ppm of phenol, 50 ppm of phenyl benzoate, and less than 0.2 ppm of benzofuran-2,3-dione.

A commercially available bisphenol A (400 g, available from Shin-nittetsu Chemical Co., Ltd.) was recrystallized from a mixture of 800 mL of toluene and 30 mL of ethanol (volume ratio: 22:1) to give a purified bisphenol A.

In a stainless steel reactor (SUS 316L) equipped with a stirrer and a distillation column were placed 22.8 weight parts of the purified bisphenol A, 22.7 weight parts of the diphenyl carbonate distillate, and a catalyst (mixture of sodium hydroxide in an amount of $2\times10^{-6}$ mol. per one mol. of the bisphenol A and tetramethylammonium hydroxide in an amount of $1\times10^{-4}$ mol. per one mol. of the bisphenol A) were placed. The mixture was degassed in vacuo at room temperature for 0.5 hour. The mixture was then heated in the reactor to carry out the polymerization reaction. The reaction mixture was kept at 230° C. and 100 mmHg for one hour after distillation of phenol began, kept at 240° C. and 100 mmHg for 0.5 hour, and kept at 255° C. and 100 mmHg for 10 minutes. The pressure was subsequently decreased from 100 mmHg to 50 mmHg for 15 minutes. The mixture was then kept under the same conditions for 15 minutes. Thus, the polycondensation reaction was carried out. The reaction mixture was subsequently heated to 270° C. and the pressure was decreased from 50 mmHg to 1 mmHg for 30 minutes. The mixture was then further kept under the conditions for one hour. After the polycondensation reaction was complete, a stabilizer (tetrabutylphosphonium dodecylbenzenesulfonate, in an amount of 2 moles per one mole of the sodium catalyst) was added to the produced polycarbonate, and they were kneaded.

Thus produced polycarbonate had a viscosity average molecular weight of 15,000 and a hue (col. b value) of 0.6.

The viscosity average molecular weight was determined by means of a Ubbelohde's viscometer in a 0.7 g/dL methylene chloride solution using the equation of $[\eta]=1.23\times10^{-4} M^{0.83}$.

The hue (b value) was determined by a reflection method by means of ND-1001 DP (available from Nippon Denshoku Industries, Co., Ltd.) using a polycarbonate pellet (2.5 mm×3.3 mm×3.0 mm). The colored value (yellow) was expressed by the b value.

Comparison Example 2

The procedures of Example 2 were repeated except for using a diphenyl carbonate distillate of Comparison Example 1 which contained 2 ppm of benzofuran-2,3-dione.

There was produced polycarbonate having a pale yellow color.

EXAMPLE 3

Diphenyl oxalate was subjected to decarbonylation reaction and the produced diphenyl carbonate was purified in the series of apparatuses illustrated in FIG. 3. In more detail, the removal of furan derivatives was carried out in the following manner.

The second distillate of Example 1 containing 2 ppm of benzofuran-2,3-dione was fed at a flow rate of approx. 43 kg/hr. into a 100 L-volume heating tank (SUS 316) which was equipped with a manifold heat exchanger having a steam circulating line. Steam was passed into the manifold heat exchanger to keep the distillate in the tank at 220° C. The distillate was stored in the tank at an average storage time of approx. 2 hours and taken out at a flow rate of approx. 43 kg/hr.

Thus heated distillate was fed into a distillation tower (height: 10 m, diameter 250 cm (A), column: Merapack 500Y, length of column: 8 m). The pressure of the top of the distillation tower was reduced to 4 kPaA, and a diphenyl carbonate distillate (diphenyl carbonate content (purity): 99.95%) containing less than approx. 0.2 ppm of benzofuran-2,3-dione was continuously collected at a rate of approx. 42 kg/hr.

Liquid chromatography analysis carried out on the diphenyl carbonate distillate confirmed that no peaks assignable to phenyl p-chlorobenzoate and diphenyl oxalate were detected.

A Hazen color value of the diphenyl carbonate distillate was lower than 5.

A portion of the diphenyl carbonate distillate was burned in the aforementioned chlorine content analytical apparatus to determine the total chlorine content. The total chlorine content was less than 0.3 ppm. Further, a portion of the diphenyl carbonate distillate was analyzed to determine the chlorine ion content by ion chromatography. The chlorine ion content was 10 ppb.

What is claimed is:

1. A composition comprising a major portion of a diaryl carbonate and benzofuran-2,3-dione which can have one or more substituents on a benzene ring moiety thereof, in an amount of not more than 1 ppm.

2. The composition of claim 1, wherein the amount of benzofuran-2,3-dione is not more than 0.8 ppm.

3. The composition of claim 1, which contains a hydrolyzable halide compound in an amount of not more than 0.2 ppm in terms of a halogen atom content.

4. The composition of claim 1, which contains an organic halide compound other than a hydrolyzable halide compound in an amount of not more than 10 ppm in terms of halogen content.

5. The composition of claim 4, wherein the organic halide is phenyl p-chlorobenzoate.

6. The composition of claim 1, which is derived from a reaction mixture of decarbonylation reaction of a diaryl oxalate.

7. The composition of claim 6, which contains a diaryl oxalate in an amount of not more than 2,000 ppm.

8. The composition of claim 1, which comprises the diaryl carbonate in an amount of not less than 98.0 wt. %.

9. The composition of claim 6, wherein the diaryl oxalate is diphenyl oxalate and the diaryl carbonate is diphenyl carbonate.

10. A process for preparing the composition of claim 1 from a reaction mixture of decarbonylation of a diaryl oxalate, which comprises the steps of:

recovering from the reaction mixture of decarbonylation, a first distillate comprising a diaryl carbonate, a by-produced benzofuran-2,3-dione, an unreacted diaryl oxalate, and other by products, by distillation;

recovering from the first distillate, a second distillate comprising the diaryl carbonate in an amount of not less than 95.0 wt. %, the benzofuran-2,3-dione in an amount of 1 to 2,000 ppm, and the unreacted diaryl oxalate in an amount of not more than 1 wt. 5, by distillation; and removing from the second distillate at least a portion of the benzoftiran-2,3-dione.

11. The process of claim 10, wherein the removal of at least a portion of the benzofuran-2,3-dione is performed by removing a distillate containing a relatively large amount of the benzofuran-2,3-dione from the second distillate, leaving a portion containing a relatively large amount of the diaryl carbonate and a relatively small amount of the benzofuran-2,3-dione.

12. The process of claim 10, wherein the removal of at least a portion of the benzofuran-2,3-dione is performed by heating the second distillate to decompose, condensate or modify at least a portion of the benzofuran-2,3-dione and removing a product of decomposition, condensation or modification, by distillation.

13. The process of claim 10, wherein the decarbonylation reaction of a diaryl oxalate is performed in liquid phase in the presence of an organic phosphorus compound catalyst.

14. A process for preparing polycarbonate which comprises reacting a polyhydric compound with the composition of claim 1.

15. The process of claim 14, wherein the composition contains a hydrolyzable halide compound in an amount of not more than 0.2 ppm in terms of halogen content.

16. The process of claim 14, wherein the composition contains an organic halide other than a hydrolyzable halide compound in an amount of not more than 10 ppm in terms of halogen content.

17. The process of claim 10, wherein the organic halide is phenyl p-chlorobenzoate.

18. The process of claim 14, wherein the composition is derived from a reaction mixture of decarbonylation reaction of a diaryl oxalate.

19. The process of claim 18, wherein the composition contains a diaryl oxalate in an amount of not more than 2,000 ppm.

20. The process of claim 14, wherein the composition comprises the diaryl carbonate in an amount of not less than 98.0 wt. %.

* * * * *